United States Patent
Pahl et al.

(10) Patent No.: US 7,381,729 B2
(45) Date of Patent: Jun. 3, 2008

(54) 4-(4-TRANS-HYDROXYCYCLOHEXYL)-AMINO-2-PHENYL-7H-PYRROLO [2,3D] PYRIMIDINE HYDROGEN MESYLATE, ITS POLYMORPHIC FORMS, AND METHODS FOR MAKING SAME

(75) Inventors: Axel Pahl, Lindwedel (DE); Timo Heinrich, Gross-Umstadt (DE); Emil Finner, Isernhagen (DE); Bernd-Martin Luitjens, Hannover (DE); Jan Zorgdrager, Zaandam (NL); Pieter C. Verveer, Utrecht (NL)

(73) Assignee: Solvay Pharmaceuticals B.V., Weesp (NL)

( * ) Notice: Subject to any disclaimer, the term of this patent is extended or adjusted under 35 U.S.C. 154(b) by 534 days.

(21) Appl. No.: 10/828,650

(22) Filed: Apr. 21, 2004

(65) Prior Publication Data

US 2004/0248912 A1 Dec. 9, 2004

Related U.S. Application Data

(60) Provisional application No. 60/464,422, filed on Apr. 22, 2003.

(51) Int. Cl.
C07D 487/04 (2006.01)
A61K 31/519 (2006.01)
A61P 9/04 (2006.01)
A61P 13/12 (2006.01)
A61P 9/12 (2006.01)

(52) U.S. Cl. .................... 514/265.1; 544/280

(58) Field of Classification Search ............... 544/280; 514/265.1
See application file for complete search history.

(56) References Cited

U.S. PATENT DOCUMENTS 6,878,716 B1 * 4/2005 Castelhano et al. ...... 514/265.1

FOREIGN PATENT DOCUMENTS

WO 1999/62518 12/1999
WO 2004/094428 11/2004

OTHER PUBLICATIONS

Engel et al. (Inter. J. Pharm., 2000, 198(2). 239-247.*
Bernstein et al., Concomitant Polymorphs, Angew. Chem. Int. Ed., vol. 38 (1999) p. 3440-3461.
Threlfall, Analysis of Organic Polymorphs: A Review, Analyst, vol. 120 (Oct. 1995) p. 2435-2460.
International Preliminary Report on Patentability, PCT/EP2004/050573 (Jul. 14, 2005).
Written Opinion of the International Searching Authority, PCT/EP2004/050573 (Received Jul. 14, 2004).

* cited by examiner

Primary Examiner—Brenda L. Coleman
Assistant Examiner—Susanna Moore
(74) Attorney, Agent, or Firm—Mayer Brown LLP

(57) ABSTRACT

The present invention relates to the novel compound 4-(4-trans-hydroxycyclohexyl)amino-2-phenyl-7H-pyrrolo[2,3d] pyrimidine hydrogen mesylate, the polymorphic α and β forms thereof, and a method for the production of said compounds.

17 Claims, 6 Drawing Sheets

Figure 1: XRPD pattern of polymorphic form α of 4-(4-*trans*-hydroxy-cyclohexyl)amino-2-phenyl-7*H*-pyrrolo[2,3d]pyrimidine mesylate
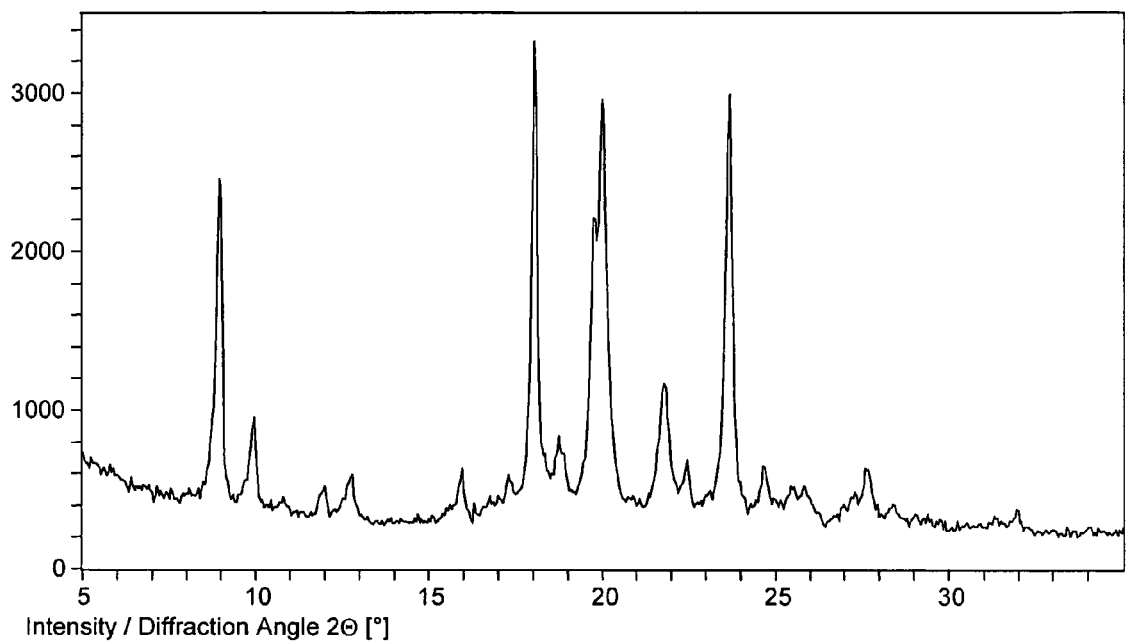

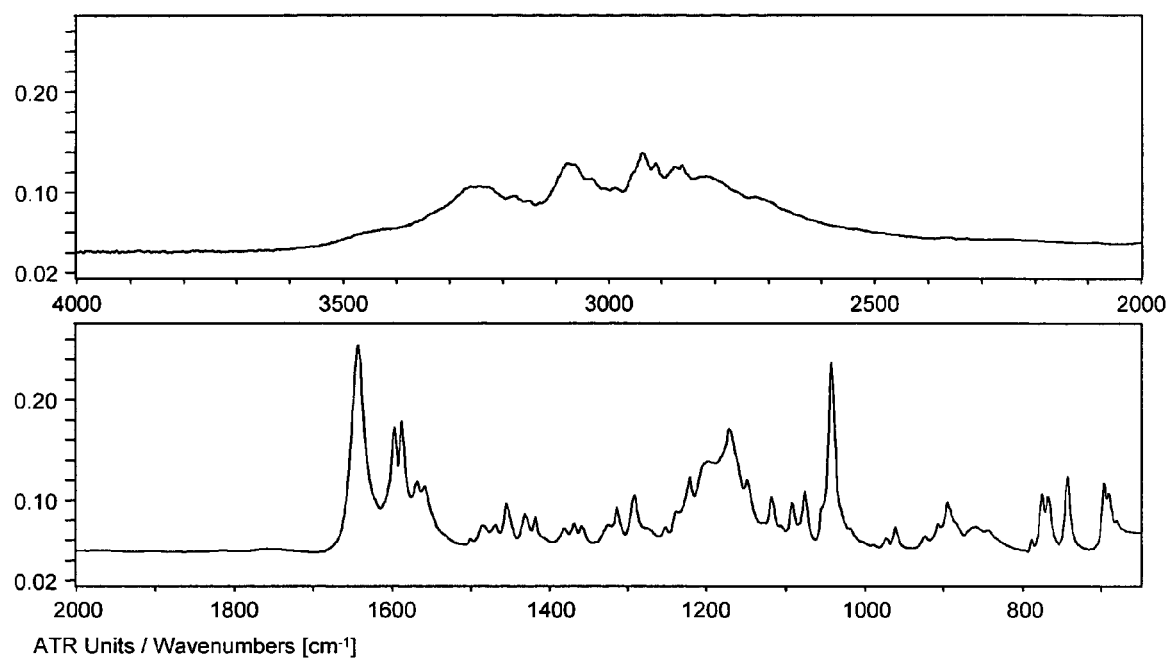
Figure 2: IR (ATR) spectrum of form polymorphic form α of 4-(4-*trans*-hydroxy-cyclohexyl)amino-2-phenyl-7*H*-pyrrolo[2,3d]pyrimidine mesylate Figure 3: DSC trace of form polymorphic form α of 4-(4-*trans*-hydroxy-cyclohexyl)amino-2-phenyl-7*H*-pyrrolo[2,3d]pyrimidine mesylate
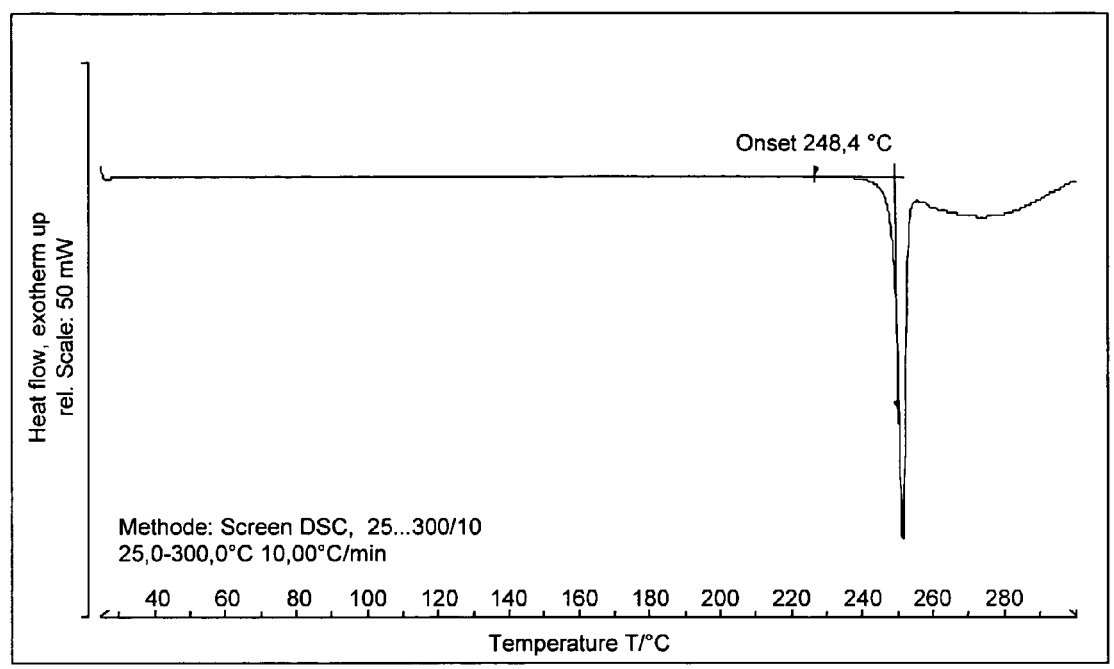

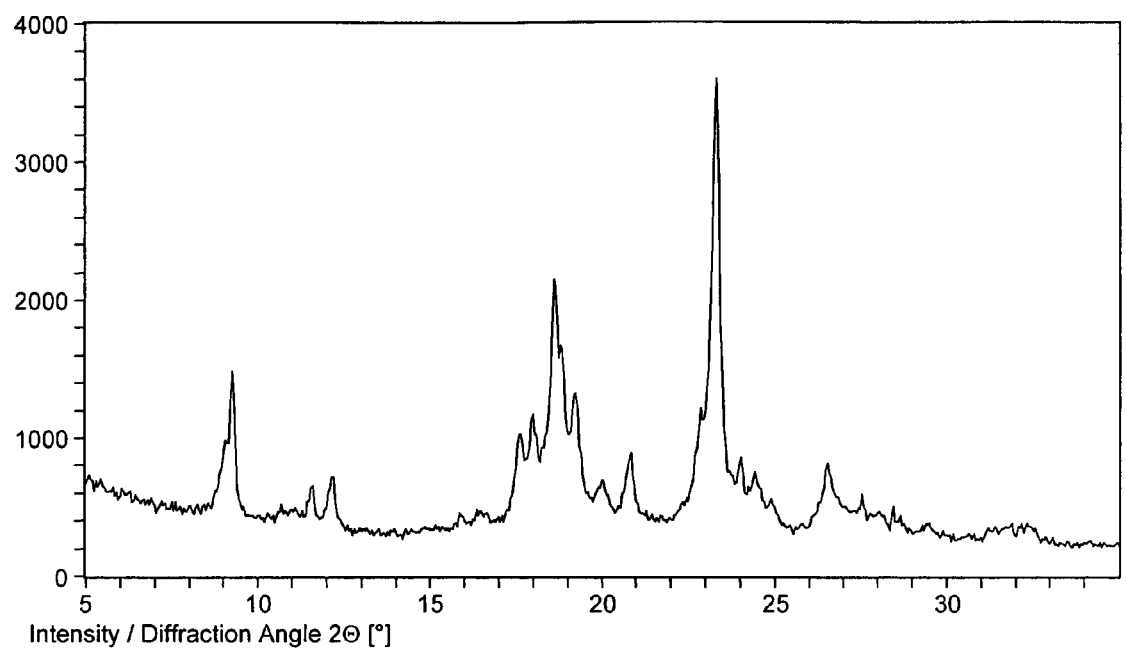
Figure 4: XRPD pattern of polymorphic form β of 4-(4-*trans*-hydroxy-cyclohexyl)amino-2-phenyl-7*H*-pyrrolo[2,3d]pyrimidine mesylate

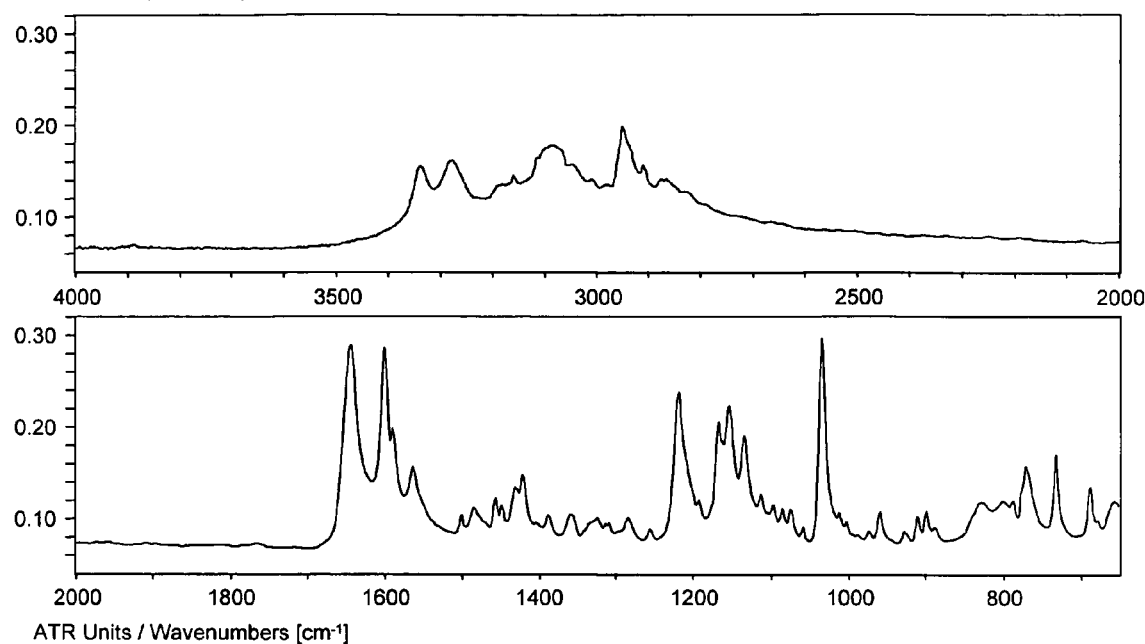
Figure 5: IR (ATR) spectrum of polymorphic form β of 4-(4-*trans*-hydroxy-cyclohexyl)amino-2-phenyl-7*H*-pyrrolo[2,3d]pyrimidine mesylate Figure 6: DSC trace of polymorphic form β of 4-(4-*trans*-hydroxy-cyclohexyl)amino-2-phenyl-7*H*-pyrrolo[2,3d]pyrimidine mesylate
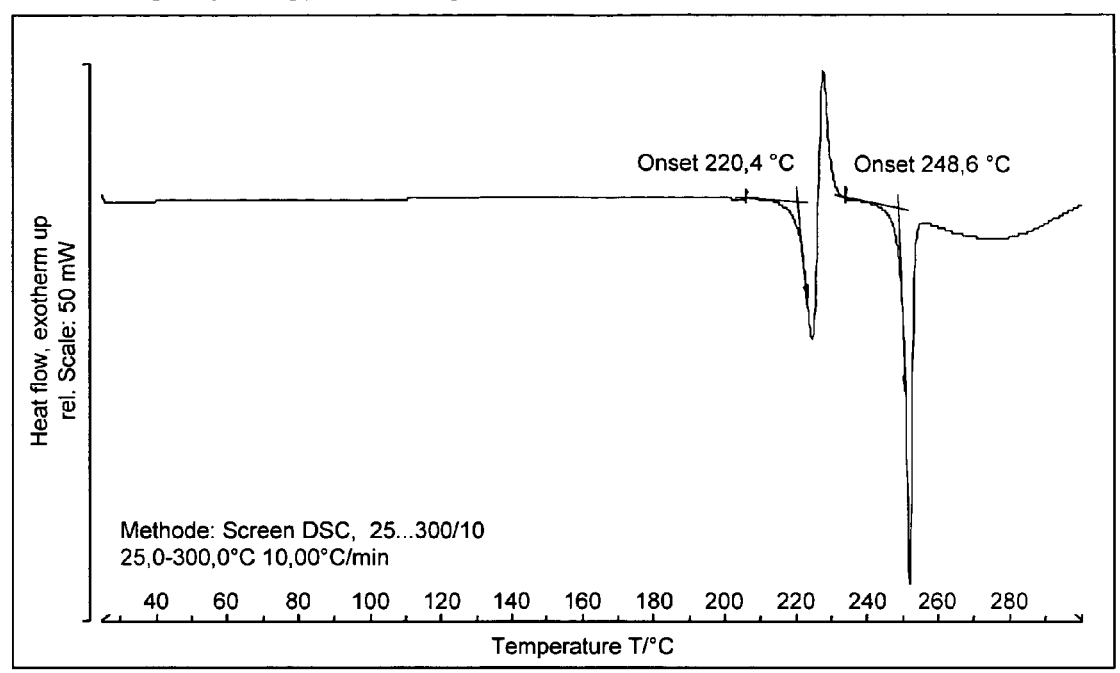

4-(4-TRANS-HYDROXYCYCLOHEXYL)-AMINO-2-PHENYL-7H-PYRROLO [2,3D] PYRIMIDINE HYDROGEN MESYLATE, ITS POLYMORPHIC FORMS, AND METHODS FOR MAKING SAME

RELATED APPLICATIONS

This application claims priority to U.S. Provisional Appl. No. 60/464,422 filed Apr. 22, 2003, and European Patent Appl. No. 03101093.7, filed Apr. 22, 2003, which are incorporated herein in their entirety.

FIELD OF THE INVENTION

The present invention relates to the novel compound 4-(4-trans-hydroxycyclohexyl) amino-2-phenyl-7H-pyrrolo [2,3d]pyrimidine hydrogen mesylate, different polymorphic forms thereof, and a method for the production of said compounds.

BACKGROUND OF THE INVENTION 4-(4-trans-hydroxycyclohexyl)amino-2-phenyl-7H-pyrrolo[2,3d]pyrimidine is disclosed in WO 99/62518 (compound 18 on page 53) and is a selective Adenosine-1 Receptor agonist that may be used in the treatment of essential hypertension, congestive heart failure, and renal failure. During further development of said compound in the above-mentioned indications, it appeared that the compound as disclosed in WO 99/62518 has the serious drawback of a low solubility in gastrointestinal fluids.

SUMMARY OF THE INVENTION

The present invention provides pharmaceutical compositions comprising a salt of 4-(4-trans-hydroxy-cyclohexyl) amino-2-phenyl-7H-pyrrolo[2,3d]pyrimidine. It is an object of the present invention to provide a salt of 4-(4-trans-hydroxy-cyclohexyl)amino-2-phenyl-7H-pyrrolo[2,3d]pyrimidine that is a crystalline, homogeneous, and stable product that has superior solubility properties.

This object can be achieved, according to the present invention, by the hydrogen mesylate salt of 4-(4-trans-hydroxy-cyclohexyl)amino-2-phenyl-7H-pyrrolo[2,3d]-pyrimidine. In the framework of the present application, this compound is further referred to as 4-(4-trans-hydroxy-cyclohexyl)amino-2-phenyl-7H-pyrrolo[2,3d]-pyrimidine mesylate. The compound has the following structure:

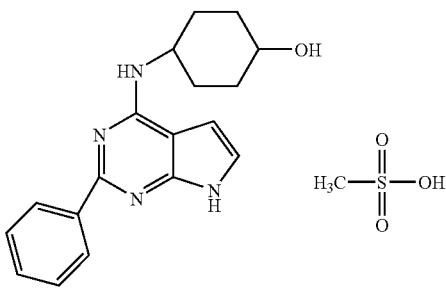

In one embodiment, the compositions of the invention are a pharmaceutical dosage form (e.g., parenteral solution, tablet, powder, capsule, gel, cream, ointment, transdermal patch, inhalant solution or suspension, or oral solution or suspension.)

BRIEF DESCRIPTION OF THE FIGURES

FIG. 1 is a line graph illustrating the X-ray powder diffraction ("XRPD") pattern of polymorphic form α of 4-(4-trans-hydroxy-cyclohexyl)amino-2-phenyl-7H-pyrrolo [2,3d]pyrimidine mesylate.

FIG. 2 is a line graph illustrating the infrared ("IR") spectrum, recorded in attenuated total reflectance ("ATR"), of polymorphic form α of 4-(4-trans-hydroxy-cyclohexyl) amino-2-phenyl-7H-pyrrolo[2,3d]pyrimidine mesylate.

FIG. 3 is a line graph illustrating the differential scanning calorimeter ("DSC") trace of polymorphic form α of 4-(4-trans-hydroxy-cyclohexyl)amino-2-phenyl-7H-pyrrolo[2,3d]pyrimidine mesylate.

FIG. 4 is a line graph illustrating the XRPD pattern of polymorphic form β of 4-(4-trans-hydroxy-cyclohexyl) amino-2-phenyl-7H-pyrrolo[2,3d]pyrimidine mesylate.

FIG. 5 is a line graph illustrating the IR spectrum, recorded in ATR, of polymorphic form β of 4-(4-trans-hydroxy-cyclohexyl)amino-2-phenyl-7H-pyrrolo[2,3d]pyrimidine mesylate.

FIG. 6 is a line graph illustrating the DSC trace of polymorphic form β of 4-(4-trans-hydroxy-cyclohexyl) amino-2-phenyl-7H-pyrrolo[2,3d]pyrimidine mesylate.

DETAILED DESCRIPTION OF THE INVENTION

The composition of the present invention broadly relates to the salts of 4-(4-trans-hydroxycyclohexyl)amino-2-phenyl-7H-pyrrolo[2,3d]pyrimidine. In contrast to the camphorsulfonate, mono-ethanedisulfonate, mono-isethionate, phosphate and sulfate salts, the mesylate salt is highly soluble in water. Further, 4-(4-trans-hydroxy-cyclohexyl)amino-2-phenyl-7H-pyrrolo[2,3d]-pyrimidine mesylate appears to be very stable at ambient conditions.

Crystalline 4-(4-trans-hydroxy-cyclohexyl)amino-2-phenyl-7H-pyrrolo[2,3d]pyrimidine mesylate was found to exist in two polymorphic forms, further indicated as polymorphic forms α and β. Both polymorphic forms have improved solubility, although form α has a better solubility than form β. Form α is metastable with respect to form β. Form β is the currently known stable form.

Substantially pure form α can be obtained in a laboratory setting by adding a solution of methane sulfonic acid in methanol to a suspension of 4-(4-trans-hydroxy-cyclohexyl) amino-2-phenyl-7H-pyrrolo[2,3d]pyrimidine in methanol, followed by the addition of isopropanol. Substantially pure form β can be obtained by adding a solution of methane sulfonic acid in ethanol to a solution of 4-(4-trans-hydroxy-cyclohexyl)amino-2-phenyl-7H-pyrrolo[2,3d]pyrimidine in ethanol, followed by the addition of water and stirring. The pure form β can also be obtained by stirring samples of pure form α in a mixture of ethanol and water. The term "substantially pure" means a purity of at least about 75%, or about 80%, or about 85%, or about 90%, or about 95%, or about 97%, or about 99%, or about 100% weight-to-weight of the composition.

The polymorphic form α of 4-(4-trans-hydroxy-cyclohexyl)amino-2-phenyl-7H-pyrrolo[2,3d]pyrimidine mesylate, according to the present invention, is defined by the following physicochemical characteristics:
(i) An XRPD pattern having characteristic reflexes (expressed in degrees of diffraction angle 2θ) at approximately: 9.0, 10.0, 12.8, 15.9, 18.1, 18.8, 19.8, 20.1, 21.8, 23.7. Diffraction angles are indicated as mean values (±0.1°) of six independent measurements. The complete XRPD pattern for the polymorphic form α is shown in FIG. 1.
(ii) An IR spectrum, recorded in ATR, having characteristic absorption bands expressed in reciprocal centimeters at approximately: 3246, 1644, 1455, 1381, 1368, 1292, 1117, 1092, 1042, 743. The complete IR spectrum for the polymorphic form α is shown in FIG. 2.
(iii) A melting point at approximately 248° C. (onset temperature) measured by DSC. The complete DSC trace for the polymorphic form α is shown in FIG. 3.

The polymorphic form β of 4-(4-trans-hydroxy-cyclohexyl)amino-2-phenyl-7H-pyrrolo[2,3d]pyrimidine mesylate, according to the present invention, is defined by the following physicochemical characteristics:
(i) An XRPD pattern having characteristic reflexes (expressed in degrees of diffraction angle 2θ) at approximately: 9.3, 11.6, 12.2, 17.6, 18.0, 18.6, 19.3, 20.8, 23.4, 26.5. Diffraction angles are indicated as mean values (±0.1°) of four independent measurements. The complete XRPD pattern for the polymorphic form β is shown in FIG. 4.
(ii) An IR spectrum, recorded in ATR, having characteristic absorption bands expressed in reciprocal centimeters at approximately: 3338, 3279, 1602, 1564, 1389, 1219, 1154, 1134, 1034, 732. The complete IR spectrum for the polymorphic form β is shown in FIG. 5.
(iii) A melting point at approximately 220° C. (onset temperature) measured by DSC. The complete DSC trace for the polymorphic form β is shown in FIG. 6.

4-(4-trans-hydroxycyclohexyl)amino-2-phenyl-7H-pyrrolo[2,3d]pyrimidine is known to be useful in treating and/or preventing essential hypertension, congestive heart failure, and renal failure in mammals. 4-(4-trans-hydroxycyclohexyl)amino-2-phenyl-7H-pyrrolo[2,3d]pyrimidine can also be administered as its hydrogen mesylate salt. Preferably, compositions of the present invention are administered in a therapeutically effective amount.

The term, "therapeutically effective amount," as used herein refers to an amount of compound that is sufficient to elicit the required or desired therapeutic and/or prophylactic response, as the particular treatment context may require. It will be understood that a therapeutically effective amount of a drug for a subject is dependent inter alia on the body weight of the subject, the age of a subject, the severity of the subject's symptoms, the subject's response to the compound, and the route of administration.

In one embodiment, the therapeutically effective amount of the compound for a subject is a dosage in the range of from about 0.01 to about 200 mg per kilogram body weight per day. In another embodiment, the therapeutically effective amount of the compound for a subject is a dosage in the range of from about 0.1 to about 100 mg per kilogram body weight per day. Such amounts maybe administered in single or divided daily doses.

A "subject" herein to which the compositions of the present invention can be administered includes a human subject of either sex and of any age, and also includes any nonhuman animal, particularly a domestic or companion animal, illustratively a cat, dog, monkey, lemur, or a horse.

The "route of administration" comprises administering the compositions of the present invention either orally, transdermally, or parenterally, and any combination thereof.

In a preferred embodiment, a therapeutically effective amount of the compound is administered parenterally to treat acute heart failure.

Compositions according to the present invention intended for oral, transdermal and/or parenteral administration may be prepared according to any method known in the art for the manufacture of pharmaceutical compositions. Such compositions may comprise one or more materials selected from the group consisting of coloring agents, flavoring agents, sweetening agents, and preservatives.

Formulations for oral use may, among other things, be tablets that contain the active ingredient in admixture with pharmaceutically acceptable excipients, such as binding agents (e.g., starch, acacia, gelatin), lubricating agents (e.g., stearic acid, magnesium stearate, talc), granulating and disintegrating agents (e.g., corn starch, alginic acid), and inert diluents (e.g., calcium phosphate, sodium phosphate, calcium carbonate, sodium carbonate, lactose). Moreover, formulations for oral use may also be soft gelatin capsules wherein the active ingredient is mixed with water or an oily medium such as liquid paraffin, peanut oil, or olive oil or hard gelatin capsules wherein the active ingredient is mixed with an inert solid diluent such as kaolin, calcium carbonate, or calcium phosphate.

The following examples are only intended to further illustrate the invention in more detail, and therefore, these examples are not deemed to restrict the scope of the invention in any way.

EXAMPLE 1

Preparation of Polymorphic Form α of 4-(4-trans-hydroxy-cyclohexyl)amino-2-phenyl-7H-pyrrolo[2,3d]pyrimidine Mesylate 701 g of 4-(4-trans-hydroxy-cyclohexyl)amino-2-phenyl-7H-pyrrolo[2,3d]pyrimidine prepared according to the method described in WO 99/62518 are suspended in 4.5 L methanol. A solution of 240 g methane sulfonic acid in 750 mL methanol is added under stirring, leading to a clear solution. The mixture is concentrated to 1900 g, then 5.5 L isopropanol are added at room temperature and the mixture is stirred for 44 h. The product is filtrated, washed four times with 0.5 L isopropanol each, and dried for 40 h at 95° C. in a vacuum drying oven to give 780 g of the title compound as crystalline modification α.

EXAMPLE 2

Preparation of Polymorphic Form α of 4-(4-trans-hydroxy-cyclohexyl)amino-2-phenyl-7H-pyrrolo[2,3d]pyrimidine Mesylate 2.00 g of 4-(4-trans-hydroxy-cyclohexyl)amino-2-phenyl-7H-pyrrolo[2,3d]pyrimidine (=6.50 mmol) was dissolved in 70 mL of acetone at reflux temperature. Under stirring at reflux temperature there was added a solution of 0.62 g of methanesulfonic acid (=6.50 mmol) in 7 mL of acetone. The reaction mixture was stirred at reflux temperature for 10 minutes. After this the reaction mixture was cooled to room temperature by removing the heating mantle. The resulting suspension was stirred for 1 hour at 2° C. The product was collected by filtration, washed twice with 5 mL of acetone, and dried under vacuo at 50° C. for 24 hours. This gave 2.49 g of crystalline modification α (=95% c/c).

The polymorphic form α was also obtained from the solvents, acetonitrile and 2-butanone, according to a similar procedure.

EXAMPLE 3

Preparation of Polymorphic Form β of 4-(4-trans-hydroxy-cyclohexyl)amino-2-phenyl-7H-pyrrolo[2,3d]pyrimidine Mesylate 2.00 g of 4-(4-trans-hydroxy-cyclohexyl)amino-2-phenyl-7H-pyrrolo[2,3d]pyrimidine (=6.50 mmol) was dissolved in a mixture of 45 mL of acetone and 5 mL of water at reflux temperature. Under stirring at reflux temperature there was added a solution of 0.62 g of methanesulfonic acid (=6.50 mmol) in 5 mL of acetone. The reaction mixture was stirred at reflux temperature for 10 minutes. The reaction mixture was then cooled to room temperature by removing the heating mantle. The resulting suspension was stirred for 45 hours at room temperature. The product was collected by filtration, washed twice with 5 mL of acetone and dried under vacuo at 50° C. for 24 hours. This gave 2.26 g of crystalline modification β (=86%).

The polymorphic form β was also obtained from the solvent mixtures acetonitrile/water and 2-butanone/water, according to a similar procedure.

EXAMPLE 4

Rearrangement of Polymorphic Form α of 4-(4-trans-hydroxy-cyclohexyl)amino-2-phenyl-7H-pyrrolo[2,3d]pyrimidine Mesylate into its Polymorphic Form β

5302 g of 4-(4-trans-hydroxy-cyclohexyl)amino-2-phenyl-7H-pyrrolo[2,3d]pyrimidine mesylate modification a was stirred in 20 L of ethanol and 2 L of water for 5 days at ambient temperature. The product was filtrated and dried at 70° C. for 40 h in a circulating air drier to give 3444 g of the title compound as crystalline modification β.

EXAMPLE 5

Analytical Methods

XRPD patterns were measured on a diffractometer using monochromatic CuKα radiation (tube voltage 40 kV, tube current 40 mA). IR spectra were recorded on a Fourier transform IR spectrometer in ATR (silicon crystal) with a spectral resolution of 2 cm$^{-1}$ using a deuterated triglycine sulfate detector.

Melting points were determined on a DSC apparatus as onset temperatures of the melting endotherm using 40 μL aluminum crucibles with a pierced lid. Temperature program: heating from 25° C. up to 300° C. with 10 K min$^{-1}$. $N_2$ atmosphere at a flow of 60 mL min$^{-1}$.

Solubility measurements were carried out with the shake flask method according to the OECD guideline at 25° C. (OECD Guideline for testing of chemicals, No. 105 (issued May 12, 1981)).

EXAMPLE 6

Solubility of 4-(4-trans-hydroxy-cyclohexyl)amino-2-phenyl-7H-pyrrolo[2,3d]pyrimidine and its Mesylates Polymorphic Form α and β

Measurement of the solubility of 4-(4-trans-hydroxy-cyclohexyl)amino-2-phenyl-7H-pyrrolo[2,3d]pyrimidine and its mesylates polymorphic form α and β in purified water gave the following results.

| Compound | Solubility in mg/L |
|---|---|
| Base | 0.0059 |
| Polymorph α | 77 |
| Polymorph β | 18.5 |

The contents of all cited references throughout this application are hereby expressly incorporated by reference. The practice of the present invention will employ, unless otherwise indicated, conventional techniques of pharmacology and pharmaceutics, which are within the skill of the art.

Although the invention has been described with respect to specific embodiments and examples, it should be appreciated that other embodiments utilizing the concept of the present invention are possible without departing from the scope of the invention. The present invention is defined by the claimed elements, and any and all modifications, variations, or equivalents that fall within the true spirit and scope of the underlying principles.

The invention claimed is:

1. The compound 4-(4-trans-hydroxy-cyclohexyl)amino-2-phenyl-7H-pyrrolo[2,3d]pyrimidine hydrogen mesylate.

2. The compound of claim 1, wherein the 4-(4-trans-hydroxy-cyclohexyl)amino-2-phenyl-7H-pyrrolo[2,3d]pyrimidine hydrogen mesylate is in a polymorphic form (α) exhibiting an X-ray powder diffraction pattern having characteristic reflexes (expressed in degrees of diffraction angle 2θ) at approximately: 9.0, 10.0, 12.8, 15.9, 18.1, 18.8, 19.8, 20.1, 21.8, 23.7.

3. The compound of claim 1, wherein the 4-(4-trans-hydroxy-cyclohexyl)amino-2-phenyl-7H-pyrrolo[2,3d]pyrimidine hydrogen mesylate is in a polymorphic form (α), characterized by an X-ray powder diffraction pattern shown in FIG. 1.

4. The compound of claim 1, wherein the 4-(4-trans-hydroxy-cyclohexyl)amino-2-phenyl-7H-pyrrolo[2,3d]pyrimidine hydrogen mesylate is in a polymorphic form (α), exhibiting an infrared spectrum recorded in attenuated total reflectance having characteristic absorption bands expressed in reciprocal centimeters at approximately: 3246, 1644, 1455, 1381, 1368, 1292, 1117, 1092, 1042, 743.

5. The compound of claim 1, wherein the 4-(4-trans-hydroxy-cyclohexyl)amino-2-phenyl-7H-pyrrolo[2,3d]pyrimidine hydrogen mesylate is in a polymorphic form (α), characterized by a complete infrared spectrum shown in FIG. 2.

6. The compound of claim 1, wherein the 4-(4-trans-hydroxy-cyclohexyl)amino-2-phenyl-7H-pyrrolo[2,3d]pyrimidine hydrogen mesylate is in a polymorphic form (α), exhibiting a melting point at approximately 248° C.

7. The compound of claim 1, wherein the 4-(4-trans-hydroxy-cyclohexyl)amino-2-phenyl-7H-pyrrolo[2,3d]pyrimidine hydrogen mesylate is in a polymorphic form (α), characterized by a complete differential scanning calorimeter trace shown in FIG. 3.

8. The compound of claim 1, wherein the 4-(4-trans-hydroxy-cyclohexyl)amino-2-phenyl-7H-pyrrolo[2,3d]pyrimidine hydrogen mesylate is in a polymorphic form (β), exhibiting an X-ray powder diffraction pattern having characteristic reflexes (expressed in degrees of diffraction angle 2θ) at approximately: 9.3, 11.6, 12.2, 17.6, 18.0, 18.6, 19.3, 20.8, 23.4, 26.5.

9. The compound of claim 1, wherein the 4-(4-trans-hydroxy-cyclohexyl)amino-2-phenyl-7H-pyrrolo[2,3d]pyrimidine hydrogen mesylate is in a polymorphic form (β), characterized by an X-ray powder diffraction pattern shown in FIG. 4.

10. The compound of claim 1, wherein the 4-(4-trans-hydroxy-cyclohexyl)amino-2-phenyl-7H-pyrrolo[2,3d]pyrimidine hydrogen mesylate is in a polymorphic form (β), exhibiting an infrared spectrum recorded in attenuated total reflectance having characteristic absorption bands expressed in reciprocal centimeters at approximately: 3338, 3279, 1602, 1564, 1389, 1219, 1154, 1134, 1034, 732.

11. The compound of claim 1, wherein the 4-(4-trans-hydroxy-cyclohexyl)amino-2-phenyl-7H-pyrrolo[2,3d]pyrimidine hydrogen mesylate is in a polymorphic form (β), characterized by a complete infrared spectrum shown in FIG. 5.

12. The compound of claim 1, wherein the 4-(4-trans-hydroxy-cyclohexyl)amino-2-phenyl-7H-pyrrolo[2,3d]pyrimidine hydrogen mesylate is in a polymorphic form (β), exhibiting a melting point at approximately 220° C.

13. The compound of claim 1, wherein the 4-(4-trans-hydroxy-cyclohexyl)amino-2-phenyl-7H-pyrrolo[2,3d]pyrimidine hydrogen mesylate is in a polymorphic form (β), characterized by a complete differential scanning calorimeter trace shown in FIG. 6.

14. A composition comprising at least one compound from any one of claims 1-13 and a pharmaceutically acceptable carrier.

15. The composition of claim 14, comprising an effective amount of 4-(4-trans-hydroxy-cyclohexyl)amino-2-phenyl-7H-pyrrolo[2,3d]pyrimidine hydrogen mesylate.

16. The composition of claim 15, in a parenteral dosage form.

17. A method for the treatment of a condition selected from the group consisting of essential hypertension, congestive heart failure and renal failure, comprising administering an effective amount of at least one compound from any one of claims 1-13.

* * * * *

UNITED STATES PATENT AND TRADEMARK OFFICE
CERTIFICATE OF CORRECTION

| | |
|---|---|
| PATENT NO. | : 7,381,729 B2 |
| APPLICATION NO. | : 10/828650 |
| DATED | : June 3, 2008 |
| INVENTOR(S) | : Axel Pahl et al. |

It is certified that error appears in the above-identified patent and that said Letters Patent is hereby corrected as shown below:

On the Title page of the patent Item [73] delete the following Assignee:

Solvay Pharmaceuticals B.V., Weesp (NL)

and insert the following Assignee:

Solvay Pharmaceuticals GmbH, Hannover (DE)

Signed and Sealed this

Fourth Day of November, 2008

JON W. DUDAS
*Director of the United States Patent and Trademark Office*

UNITED STATES PATENT AND TRADEMARK OFFICE
CERTIFICATE OF CORRECTION

PATENT NO.        : 7,381,729 B2                                              Page 1 of 1
APPLICATION NO.   : 10/828650
DATED             : June 3, 2008
INVENTOR(S)       : Pahl et al.

It is certified that error appears in the above-identified patent and that said Letters Patent is hereby corrected as shown below:

On the Title page,

[*] Notice:    Subject to any disclaimer, the term of this patent is extended or adjusted under 35 USC 154(b) by 534 days Delete the phrase "by 534 days" and insert -- by 633 days --

Signed and Sealed this

Thirteenth Day of July, 2010

David J. Kappos
*Director of the United States Patent and Trademark Office*